(12) United States Patent
Martinez

(10) Patent No.: US 8,932,654 B2
(45) Date of Patent: Jan. 13, 2015

(54) SWINGLEA GLUTINOSA LEAVES DERIVED MATERIAL IN COMBINATION WITH AVERMECTINS FOR CONTROL OF ACARI

(75) Inventor: Jamez Alberto Jimenez Martinez, Medellin (CO)

(73) Assignee: Ecoflora Agro S.A.S., Rionegro, Antioquia (CO)

( * ) Notice: Subject to any disclaimer, the term of this patent is extended or adjusted under 35 U.S.C. 154(b) by 681 days.

(21) Appl. No.: 12/891,841

(22) Filed: Sep. 28, 2010

(65) Prior Publication Data
US 2011/0020481 A1 Jan. 27, 2011

Related U.S. Application Data

(63) Continuation-in-part of application No. 12/466,801, filed on May 15, 2009.

(51) Int. Cl.
| | | |
|---|---|---|
| A61K 36/00 | (2006.01) | |
| A61K 36/752 | (2006.01) | |
| A01N 25/00 | (2006.01) | |
| A61K 36/75 | (2006.01) | |

(52) U.S. Cl.
CPC ..................................... A61K 36/75 (2013.01)
USPC ........................... 424/736; 424/774; 424/405

(58) Field of Classification Search
CPC .. A61K 36/75; A61K 36/774; A61K 2201/10
USPC .......................................... 424/736, 774, 405
See application file for complete search history.

(56) References Cited

U.S. PATENT DOCUMENTS

| | | | |
|---|---|---|---|
| 5,389,662 A | 2/1995 | Pap et al. | |
| 5,498,624 A * | 3/1996 | McLoughlin et al. | 514/406 |
| 5,948,805 A * | 9/1999 | Geddens et al. | 514/376 |
| 7,297,349 B2 | 11/2007 | Arimoto et al. | |
| 2002/0031538 A1 | 3/2002 | Scarmoutzos | |
| 2010/0291241 A1 | 11/2010 | Restrepo et al. | |
| 2010/0316751 A1 | 12/2010 | Jimenez Martinez et al. | |
| 2011/0059195 A1 | 3/2011 | Martinez | |

FOREIGN PATENT DOCUMENTS

WO  WO 2010/131109 A1  11/2010

OTHER PUBLICATIONS

Alvarez et al. ("Controlling powdery mildew of roses using a plant extract and foliar fertilizers", Phytopathology, (Jun. 2001), vol. 91, No. 6, Supplement, pp. 101-102).*
Alvarez, E., et al., "Controlling powdery mildew of roses using a plant extract and foliar fertilizers," *Phytopathology 91*(6):S101, 2001/APS/MSA/SON Annual Meeting, MSA Abstracts, Salt Lake City, United States.
Braga, P.A.C., et al., "In vitro cytotoxicity activity on several cancer cell lines of acridone alkaloids and N-phenylethyl-benzamide derivatives from *Swinglea glutionsa* (Bl.) Merr.," *Natural Product Research 21*(1):47-55, Taylor & Francis, England (2007).
Bueno-Sanchez, J.G. et al., "Evaluación de la actividad antimocribaceriana de algunas plantas aromáticas y medicinales que crecen en Colombia." Instituto Nacional de Salud, Grupo de Micobacterias 1, Bogotá, D.C., Centro Colombiano de Investigación en Tuberculosis CCITB, Colombia. Universidad Industrial de Santander, Bucaramanga, Centro de Investigación en Biomoléculas, CIBIMOL, CENIVAM2. Colombia. Jul. 23-28, 2008.
Dos Santos, D.A.P., et al., "Antiparasitic Activities of Acridone Alkaloids from *Swinglea glutinosa* (Bl.) Merr.," *J. Braz. Chem. Soc. 20*(4):644-659, Sociedade Brasileira de Quimica, Brazil (Nov. 2009).
Purcaro, R., et al., "Algicide Constituents from *Swinglea glutinasa*," *J. Agric. Food. Chem. 57*:10632-10635, American Chemical Society, United States (Oct. 2009).
Weniger, B., et al., "Antiprotozoal activities of Colombian plants," *Journal of Ethnopharmacology 78*(2-3):193-200, Elsevier Science Ireland, Ltd., Ireland (2001).
Weniger, B., et al., "Bioactive Acridone Alkaloids from *Swinglea glutinosa*," *J. Nat. Prod. 64*(9):1221-1223, American Chemical Society and American Society of Pharmacognosy, United States (published online Sep. 8, 2001).
Final Office Action mailed Jun. 8, 2011, in U.S. Appl. No. 12/860,896, filed Aug. 22, 2010, inventors Jimenez Martinez et al.
Non Final Office Action mailed Nov. 12, 2010, in U.S. Appl. No. 12/860,896, filed Aug. 22, 2010, inventors Jimenez Martinez et al.
Final Office Action mailed Jul. 21, 2011, in U.S. Appl. No. 12/945,873, filed Nov. 14, 2010, inventor Jimenez Martinez.
Non Final Office Action mailed Feb. 4, 2011, in U.S. Appl. No. 12/945,873, filed Nov. 14, 2010, inventor Jimenez Martinez.
Non Final Office Action mailed Jun. 3, 2014, in U.S. Appl. No. 12/945,873, filed Nov. 14, 2010, inventor Jimenez Martinez.
Final Office Action mailed May 31, 2011, in U.S. Appl. No. 12/466,801, filed May 15, 2009, inventors Toro Restrepo et al.
Non Final Office Action mailed Nov. 15, 2010, in U.S. Appl. No. 12/466,801, filed May 15, 2009, inventors Toro Restrepo et al.
Non Final Office Action mailed May 12, 2014, in U.S. Appl. No. 12/466,801, filed May 15, 2009, inventors Toro Restrepo et al.
European Patent Search Report completed Aug. 28, 2013, received Sep. 9, 2013 in European Application No. EP 10 77 4608, European Patent Office, Munich, Germany.

* cited by examiner

*Primary Examiner* — Chris R Tate
*Assistant Examiner* — Deborah Davis
(74) *Attorney, Agent, or Firm* — Sterne, Kessler, Goldstein & Fox P.L.L.C.

(57) ABSTRACT

The invention of the present application provides a natural material derived from *Swinglea glutinosa* leaves that in combination with avermectins, increases the effect of avermectins over mites. The material derived from *Swinglea glutinosa* leaves, in a preparation with avermectins, results in an all natural material with the potential to replace combinations of avermectins with synthetic pyrethroids, eliminating the need to use synthetic pesticides for acari control.

22 Claims, No Drawings

*SWINGLEA GLUTINOSA* LEAVES DERIVED MATERIAL IN COMBINATION WITH AVERMECTINS FOR CONTROL OF ACARI

This Application is a continuation in part of U.S. patent application Ser. No. 12/466,801 filed on May 15, 2009, which has one inventor in common. U.S. patent application Ser. No. 12/466,801 is incorporated herein in its entirety by reference.

BACKGROUND OF THE INVENTION

1. Area of the Invention

The present invention is related to how to treat mites material derived from *Swinglea glutinosa* leaves and a preparation made of the material derived from *Swinglea glutinosa* leaves and avermectins. The extract is described by preceding pending unpublished U.S. patent application Ser. No. 12/466,801.

2. Description of Prior Art

Mite pests affect a range of agronomic, vegetable and fruit cultivations causing great losses. Avermectin mixes, such as abamectin have been use to control mites. Because, resistance by mites to avermectins is common, increasingly high doses are being used to control these acari. In addition, in order to combat resistance, avermectins are used in combination with synthetic pesticides, e.g., pyrethroids.

Unfortunately, there is no description in the prior art of a natural derived compound that can be used in a mix with avermectins to diminish resistance by mites to avermectins, or to avoid using synthetic pyrethroids. The Invention of the present Application overcomes these prior art limitations.

SUMMARY OF THE INVENTION

The invention of the present application provides a natural material derived from *Swinglea glutinosa* leaves that in combination with avermectins, increases the effect of avermectins over mites. The material derived from *Swinglea glutinosa* leaves, in a preparation with avermectins, results in an all natural material with the potential to replace combinations of avermectins with synthetic pyrethroids, eliminating the need to use synthetic pesticides for acari control.

More specifically, the invention of the present application provides a preparation that comprises a material derived from *Swinglea glutinosa* leaves and avermectins.

In an aspect of the present invention, the preparation is used to treat acari.

In one additional aspect of the present invention, the acari is *Tetranichus* sp.

In another aspect of the present invention, the avermectins of the preparation are constituted by abamectin.

In one more aspect of the preparation of the present invention, the material derived from *Swinglea glutinosa* leaves is an extract obtained by a method comprising:

A. Exposing bright dark green *Swinglea glutinosa* leaves in a dry environment, wherein said leaves are protected from direct sunlight, wherein the leaves are exposed to air flow;
B. leaving the leaves in the environment described in A. until the leaves turn opaque green and the leaves are brittle;
C. breaking up the leaves into small fragments;
D. putting the *Swinglea glutinosa* leaf fragments in contact with a solvent at least once;
E. repeat step D. until the solvent is enriched with substances derived from the leaf fragments; and,
F. retiring the solvent to release an extract.

Objectives and advantages of the present Application invention will be more evident in the detailed description of the invention and the claims.

DETAILED DESCRIPTION OF THE INVENTION the invention of the present application provides a preparation that comprises a material derived from *Swinglea glutinosa* leaves and avermectins.

In an aspect of the present invention, the preparation is used to treat acari.

In one additional aspect of the present invention, the acari is *Tetranichus* sp.

In another aspect of the present invention, the avermectins of the preparation are constituted by abamectin.

In one more aspect of the preparation of the present invention, the material derived from *Swinglea glutinosa* leaves is an extract obtained by a method comprising:

A. Exposing bright dark green *Swinglea glutinosa* leaves in a dry environment, wherein said leaves are protected from direct sunlight, wherein the leaves are exposed to air flow;
B. leaving the leaves in the environment described in A. until the leaves turn opaque green and the leaves are brittle;
C. breaking up the leaves into small fragments;
D. putting the *Swinglea glutinosa* leaf fragments in contact with a solvent at least once;
E. repeat step D. until the solvent is enriched with substances derived from the leaf fragments; and,
F. retiring the solvent to release an extract.

The term acari includes:
*Polyphagotarsonemus* sp.
*Aculops* sp.
*Brevipalpus* sp.
*Aceria* sp.
*Phyllocoptruta* sp.
*Epitrimerus* sp.
*Tetranychus* sp.
*Panonychus* sp.
*Phyllocnistis* sp.
*Liriomyza* sp.
*Scrobipalpula* sp.
*Psylla* sp.
*Boophilus* sp.,
and other species describe as acari.

In one more aspect of the *Swinglea glutinosa* extract of the present invention, in the method, the leaves must not be broken into leaf fragments that are less than 0.5 mm, since smaller fragments would tend to become a single mass which will become a limitation for the optimal extraction with a solvent.

In all cases where a solvent is mentioned in this application, the solvent that can be used comprises ethanol, methanol, hexane, propanol, isopropanol, $CO_2$, acetone, water, ethyl-acetate, nitrile-acetate, toluene, tetrahydrofurane, Chloroform, dichloromethane, and others.

Objectives and advantages of the present Application invention will be more evident in the detailed description of the invention and the claims.

EXAMPLES

A test was made by putting 5 mm discs cut from leaves of bean plants in Petri plates, wherein a the 5 mm leaf discs were bathed with: 1) Water only; 2) 2 ml of *Swinglea glutinosa* Extract/Liter; 3) a solution of a preparation made of 2 ml of

*Swinglea glutinosa* Extract/Liter+abamectin 0.1 to 0.3 ml/Liter; and 4) Abamectin 0.1 to 0.3 ml/Liter. 10 *Tetranichus* sp. individual mites were put on top of each of the 5 mm leaf discs. Water surrounded the 5 mm leaf discs in the Petri plates to avoid the mites from escaping the discs. Mortality of *Tetranichus* sp. mites was measured after 24 hours and 48 hours. All the experiments were repeated three times and each experiment consisted in a set of three Petri plates for each variable for a total of 24 plates per experiment.

The results are shown in the following Table:

TABLE 1

Mortality of *Tetranichus* sp. Mites

| TREATMENT | Average percentage Mortality 24 hours | Average percentage Mortality 48 hours |
|---|---|---|
| Water | 5.9% | 10.1% |
| SS | 9.3% | 12.4% |
| SS + 0.1 Aba | 15.0% | 17.2% |
| Aba 0.1 | 6.7% | 6.7% |
| SS + 0.2 Aba | 8.3% | 18.3% |
| 0.2 Aba | 8.3% | 10.0% |
| SS + 0.3 Aba | 18.3% | 26.7% |
| 0.3 Aba | 0.0% | 5.7% |

SS = *Swinglea glutinosa* extract 2 ml/L
Aba = Abamectin ml/L

Table 1. shows that in all cases, the preparation with *Swinglea glutinosa*+ abamectin combination resulted in a higher mite mortality than the mite mortality when abamectin was used alone.

In conclusion, these results suggest that the use of *Swinglea glutinosa* in combination with abamectin to control mites is better than abamectin alone at 0.1 to 0.3 doses.

The invention claimed is:

1. An acaricide preparation for use in killing acari comprising effective amounts of (i) an extract isolated from *Swinglea glutinosa* leaves and (ii) an avermectin, wherein the *Swinglea glutinosa* extract is obtained by a method comprising contacting *Swinglea glutinosa* leaves with a solvent consisting essentially of a water:organic solvent mixture.

2. The acaricide preparation of claim 1, wherein the acari belongs to the genus *Polyphagotarsonemus, Aculops, Brevipalpus, Aceria, Phyllocoptruta, Epitrimerus, Panonychus, Phyllocnistis*, or *Tetranichus*.

3. The acaricide preparation according to claim 1, wherein the avermectin is an avermectin mix.

4. The acaricide preparation according to claim 3, wherein the avermectin mix is abamectin.

5. The acaricide preparation according to claim 1, further comprising a pyrethroid.

6. The acaricide preparation according to claim 5, wherein the pyrethroid is a synthetic pyrethroid.

7. The acaricide preparation according to claim 1, further comprising camphor, garlic oil, orange oil, lemon oil, lime oil, *Cymbopogon* sp. oil, *Eugenia caryophyllata* oil, *Eucalyptus* sp. oil, *Melaleuca alternifolia* oil, *Citrus sinensis* oil, *Citrus* sp. oil, cinnamon oil, or combinations thereof.

8. A method for the production of an acaricide preparation comprising an extract isolated from *Swinglea glutinosa* leaves and an avermectin, wherein the method comprises:
(a) contacting *Swinglea glutinosa* leaves with a solvent consisting essentially of a water:organic solvent mixture; and,
(b) combining the *Swinglea glutinosa* extract with an avermectin.

9. The method according to claim 8, wherein the avermectin is an avermectin mix.

10. The method according to claim 9, wherein the avermectin mix is abamectin.

11. The method according to claim 8, further comprising a pyrethroid.

12. The method according to claim 11, wherein the pyrethroid is a synthetic pyrethroid.

13. The method according to claim 8, wherein the leaves are leaf fragments.

14. The method according to claim 13, wherein the fragments are larger than 0.05 mm.

15. The method according to claim 8, wherein the organic solvent is water-miscible.

16. The method according to claim 8, wherein the organic solvent is not water-miscible.

17. The method according to claim 8, wherein the organic solvent is selected from the group consisting of ethanol, methanol, hexane, propanol, isopropanol, acetone, ethyl-acetate, nitrile-acetate, toluene, tetrahydrofurane, chloroform, dichloromethane, and combinations thereof.

18. The method according to claim 8, wherein the organic solvent is ethanol.

19. The method according to claim 8, wherein the *Swinglea glutinosa* extract's mass comprises about 60% of the initial leaf mass.

20. The method according to claim 18, wherein the water:ethanol ratio is about 70:320.

21. A method of killing an acari comprising contacting the acari with an effective amount of the acaricide preparation according to claim 1.

22. The method according to claim 21, wherein the acari belongs to the genus *Polyphagotarsonemus, Aculops, Brevipalpus, Aceria, Phyllocoptruta, Epitrimerus, Panonychus, Phyllocnistis*, or *Tetranichus*.

* * * * *